United States Patent
Hwang et al.

(10) Patent No.: US 8,540,630 B2
(45) Date of Patent: Sep. 24, 2013

(54) METHOD AND MEDIUM FOR SYNCHRONIZING VITAL SIGNAL DATA RECEIVED FROM PLURAL MEASURING APPARATUSES AND SYSTEM OF ENABLING THE METHOD

(75) Inventors: Jin Sang Hwang, Suwon-si (KR); Soo Kwan Kim, Seongnam-si (KR); Kyung Ho Kim, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1440 days.

(21) Appl. No.: 11/519,952

(22) Filed: Sep. 13, 2006

(65) Prior Publication Data

US 2007/0135692 A1      Jun. 14, 2007

(30) Foreign Application Priority Data

Dec. 13, 2005   (KR) ........................ 10-2005-0122232

(51) Int. Cl.
```
A61B 5/00      (2006.01)
G08B 1/08      (2006.01)
H04L 7/00      (2006.01)
H04L 13/10     (2006.01)
```
(52) U.S. Cl.
USPC ............. 600/301; 340/539.12; 370/305

(58) Field of Classification Search
USPC .............. 600/300, 301; 128/903–905, 920
See application file for complete search history.

(56) References Cited

U.S. PATENT DOCUMENTS

| | | | | |
|---|---|---|---|---|
| 5,807,245 A | * | 9/1998 | Aldestam et al. | 600/300 |
| 6,416,471 B1 | | 7/2002 | Kumar et al. | |
| 7,299,085 B2 | * | 11/2007 | Bergelson et al. | 600/509 |
| 7,627,811 B2 | * | 12/2009 | Thong et al. | 715/203 |
| 2004/0215089 A1 | * | 10/2004 | Bergelson et al. | 600/510 |
| 2006/0200743 A1 | * | 9/2006 | Thong et al. | 715/500.1 |
| 2009/0082635 A1 | * | 3/2009 | Baldus et al. | 600/300 |

FOREIGN PATENT DOCUMENTS

| | | |
|---|---|---|
| JP | 2004-97589 | 4/2004 |
| KR | 2001-0056530 | 7/2001 |
| KR | 2001-0062847 | 7/2001 |
| KR | 2002-0007860 | 1/2002 |
| KR | 10-2004-0084778 | 10/2004 |

* cited by examiner

*Primary Examiner* — Bill Thomson
*Assistant Examiner* — Shirley Jian
(74) *Attorney, Agent, or Firm* — Staas & Halsey LLP (57) ABSTRACT

A method of synchronizing a user's biosignal data received from a plurality of measurement devices is provided, including: transmitting a time set command to each of the plurality of measurement devices; receiving the user's first biosignal data from each of the plurality of measurement devices, the first biosignal data including a time axis and the time axis including a measurement start time and a measurement termination time; comparing the measurement start time and the measurement termination time with a standard time; and generating second biosignal data from corrected first biosignal data, corrected by referring to the standard time, when the comparison results in an error; and synchronizing a plurality of the second biosignal data and generating third biosignal data, wherein each of the plurality of measurement devices receives the time set command and generates the first biosignal data.

14 Claims, 7 Drawing Sheets

METHOD AND MEDIUM FOR SYNCHRONIZING VITAL SIGNAL DATA RECEIVED FROM PLURAL MEASURING APPARATUSES AND SYSTEM OF ENABLING THE METHOD

CROSS-REFERENCE TO RELATED APPLICATIONS

This application claims the benefit of Korean Patent Application No. 10-2005-122232, filed on Dec. 13, 2005, in the Korean Intellectual Property Office, the disclosure of which is incorporated herein by reference.

BACKGROUND OF THE INVENTION

1. Field of the Invention

The present invention relates to a method, medium, and system for synchronizing biosignal data received from a plurality of measurement devices, and more particularly, to a method, medium, and system which can initially generate second biosignal data by receiving first biosignal data from a plurality of measurement devices, and determining whether an error is included therein, and when an error is included, correcting the first biosignal data, and subsequently generate third biosignal data capable of analyzing a biosignal by synchronizing a plurality of first biosignal data.

2. Description of the Related Art

Recent developments in the field of medical science have prolonged the life span of human beings. Along with this, people's concerns about health are also increasing. Accordingly, various methods and systems for checking a user's health are being developed. As an example, a method of receiving a biosignal associated with a user's health from a measurement device attached onto the user's living body and checking the user's health has been developed.

Figure 1:
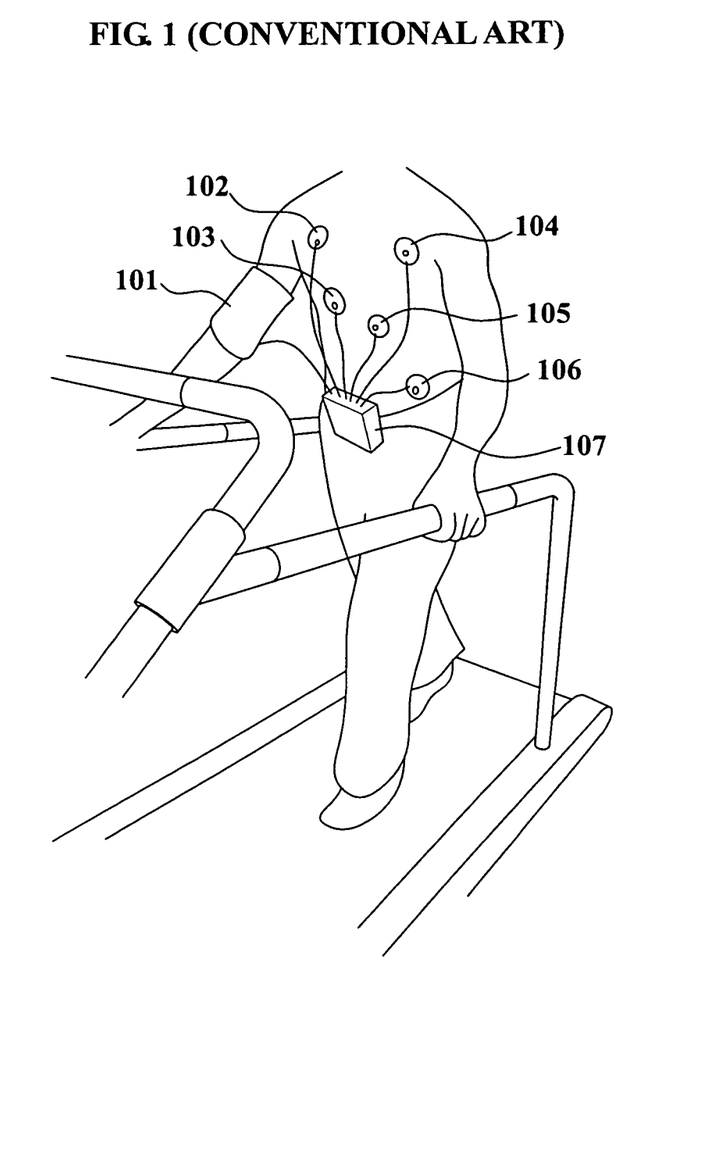
FIG. 1 is a diagram illustrating a biosignal measurement device according to the conventional art.

FIG. 1 is a diagram illustrating a biosignal measurement device according to the conventional art. Referring to FIG. 1, a plurality of measurement devices 101, 102, 103, 104, 105 and 106 being attached onto a user's living body, measures biosignals, generates biosignal data, and transmits the generated biosignal data to a data collection device 107.

The data collection device 107 analyzes the biosignal data and outputs analysis results with respect to the user's health.

In this instance, each of the plurality of measurement devices 101 to 106 is independently constructed. Each of the plurality of measurement devices 101 to 106 measures biosignals using various timings and periods, and generates biosignal data. Also, the data collection device 107 collects the biosignal data for its analysis and outputs the analysis results thereof.

However, each of the plurality of measurement devices 101 to 106 sets its reference time and generates biosignal data according to the reference time. Accordingly, it may be slower or faster than the originally set reference time according to various types of external or internal conditions.

Also, when the reference time of the measurement device is different from the originally set reference time, a measurement time of biosignal data generated in the measurement device may drift. Accordingly, biosignal data is inputted into the data collection device 107 at a time which drifts from an actual measurement time, thereby causing an error. In particular, in the case of data whose results may be accurately outputted only when simultaneously measuring and comparing the data, an error of the reference time of each measurement device may cause a very serious miscalculation.

SUMMARY OF THE INVENTION

Additional aspects, features and/or advantages of the invention will be set forth in part in the description which follows and, in part, will be apparent from the description, or may be learned by practice of the invention.

An aspect of the present invention provides a biosignal data synchronization method, medium, and system which can accurately correct an error in a reference time of a measurement device and generate synchronized biosignal data, by correcting a time error of first biosignal data received from a plurality of measurement devices, generating second biosignal data and synchronizing the second biosignal data to match in an identical time axis.

An aspect of the present invention provides a biosignal data synchronization method, medium, and system which can provide third biosignal data enabling analysis of a user's health on the basis of various pattern changes of biosignals within an identical time, by synchronizing and providing various biosignal data received from a plurality of measurement devices without a time error.

An aspect of the present invention provides a biosignal data synchronization method, medium, and system which can correct an error of a timer installed in a measurement device and set a reference time to be identical to a standard time of a biosignal data synchronization system.

According to an aspect of the present invention, there is provided a method of synchronizing a user's biosignal data received from a plurality of measurement devices, the method including: transmitting a time set command to each of the plurality of measurement devices; receiving the user's first biosignal data from each of the plurality of measurement devices, the first biosignal data including a time axis and the time axis including a measurement start time and a measurement termination time; comparing the measurement start time and the measurement termination time with a standard time; and generating second biosignal data from corrected first biosignal data, corrected by referring to the standard time, when the comparison results in an error; and synchronizing a plurality of the second biosignal data and generating third biosignal data, wherein each of the plurality of measurement devices receives the time set command and generates the first biosignal data.

According to another aspect of the present invention, there is provided a method of operating a measurement device measuring a user's biosignal and generating biosignal data, the method including: receiving a time set command from a predetermined system and, in response to receipt of the time set command, measuring the user's biosignal, and generating first biosignal data, the first biosignal data including a time axis and the time axis including a measurement start time and a measurement termination time; transmitting the generated biosignal data to the system; and receiving error data from the system and resetting a reference time of the measurement device.

According to another aspect of the present invention, there is provided a computer readable recording medium storing a program for implementing a method of synchronizing a user's biosignal data received from a plurality of measurement devices, the method including: transmitting a time set command to each of the plurality of measurement devices; receiving the user's first biosignal data from each of the plurality of measurement devices, the first biosignal data including a time axis and the time axis including a measurement start time and a measurement termination time; comparing the measurement start time and the measurement termination time with a standard time; generating second biosignal data from corrected first biosignal data, corrected by referring to the standard time, when the comparison results in an error; and generating third biosignal data by synchronizing a plurality of the second biosignal data, wherein each of the plurality of measurement devices receives the time set command and generates the first biosignal data.

According to still another aspect of the present invention, there is provided a system for synchronizing a user's biosignal data received from a plurality of measurement devices, the system including: a communication terminal transmitting a time set command to each of the plurality of measurement devices and receiving the user's first biosignal data from each of the plurality of measurement devices, the first biosignal data including a time axis and the time axis including a measurement start time and a measurement termination time; an error control module comparing the measurement start time and the measurement termination time with a standard time and, when the comparison results in an error, generating second biosignal data from corrected first biosignal data, corrected by referring to the standard time, and a data synchronization module synchronizing a plurality of the generated second biosignal data and generating third biosignal data.

According to yet another aspect of the present invention, there is provided a measurement device of measuring a user's biosignal and generating biosignal data, the device including: a biosignal data generation module receiving a time set command from a predetermined system and, in response to the received time set command, measuring the user's biosignal, and generating first biosignal data, the first biosignal data including a time axis and the time axis including a measurement start time and a measurement termination time; a communication module transmitting the generated first biosignal data to the system; and an error correction module receiving error data from the system and correcting a reference time of the measurement device, wherein the system receives the user's first biosignal data from the measurement device, the first biosignal data including a time axis and the time axis including a measurement start time and a measurement termination time, compares the measurement start time and the measurement termination time with a standard time of the system, when the comparison results in an error, generates second biosignal data from corrected measurement data, corrected by referring to the standard time, and generates error data with respect to the error and transmits the generated error data to the measurement device.

According to another aspect of the present invention, there is provided at least one computer readable medium storing instruction that control at least one processor to implement a method of operating a measurement device measuring a user's biosignal and generating biosignal data, the method including: receiving a time set command from a predetermined system and, in response to receipt of the time set command, measuring the user's biosignal, and generating first biosignal data, the first biosignal data including a time axis and the time axis including a measurement start time and a measurement termination time; transmitting the generated biosignal data to the system; and receiving error data from the system and resetting a reference time of the measurement device.

According to another aspect of the present invention, there is provided a method of synchronizing a user's biosignal data received from a plurality of measurement devices, including: transmitting a time set command to each of the plurality of measurement devices; receiving the user's first biosignal data from each of the plurality of measurement devices, the first biosignal data including a time axis and the time axis including a measurement start time and a measurement termination time; comparing the measurement start time and the measurement termination time with a standard time; and generating second biosignal data from corrected first biosignal data, corrected by referring to the standard time, when the comparison results in an error; synchronizing the second biosignal data; and generating third biosignal data based on synchronization of second biosignal data.

According to another aspect of the present invention, there is provided at least one computer readable medium storing instructions that control at least one processor to implement a method of synchronizing a user's biosignal data received from a plurality of measurement devices, the method including: transmitting a time set command to each of the plurality of measurement devices; receiving the user's first biosignal data from each of the plurality of measurement devices, the first biosignal data including a time axis and the time axis including a measurement start time and a measurement termination time; comparing the measurement start time and the measurement termination time with a standard time; generating second biosignal data from corrected first biosignal data, corrected by referring to the standard time, when the comparison results in an error; synchronizing a plurality of the second biosignal data; and generating third biosignal data based on synchronization of the plurality of second biosignal data.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION OF THE PREFERRED EMBODIMENTS

Reference will now be made in detail to exemplary embodiments of the present invention, examples of which are illustrated in the accompanying drawings, wherein like reference numerals refer to the like elements throughout. Exemplary embodiments are described below in order to explain the present invention by referring to the figures.

Figure 2:
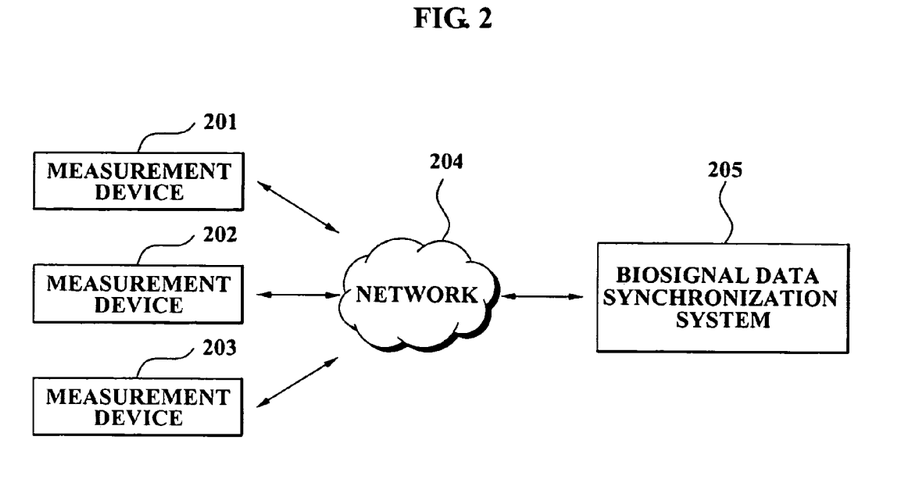
FIG. 2 is a diagram illustrating a network connection of a biosignal data synchronization system according to an exemplary embodiment of the present invention.

FIG. 2 is a diagram illustrating a network connection of a biosignal data synchronization system according to an exemplary embodiment of the present invention. Referring to FIG. 2, measurement devices 201, 202 and 203 are connected to a biosignal data synchronization system 205 via a wired/wireless network 204.

Hereinafter, as an example, the biosignal data synchronization system 205 will be described when independently constructed and operated, but the biosignal data synchronization system 205 may be included in any one of the measurement devices 201, 202 and 203, for its operation.

The measurement devices 201, 202 and 203 of the present invention include a device which measures a user's biosignal associated with the user's health, generates biosignal data, and transmits the biosignal data to the biosignal data synchronization system 205 via a predetermined communication module. A biosignal includes any type of information associated with a user's health, such as breathing, a pulse, a temperature, an electrocardiogram, activity pattern information and an activity signal. Hereinafter, an operating method of a measurement device and a biosignal data synchronization system of the present invention will be described with reference to FIG. 3.

Figure 3:
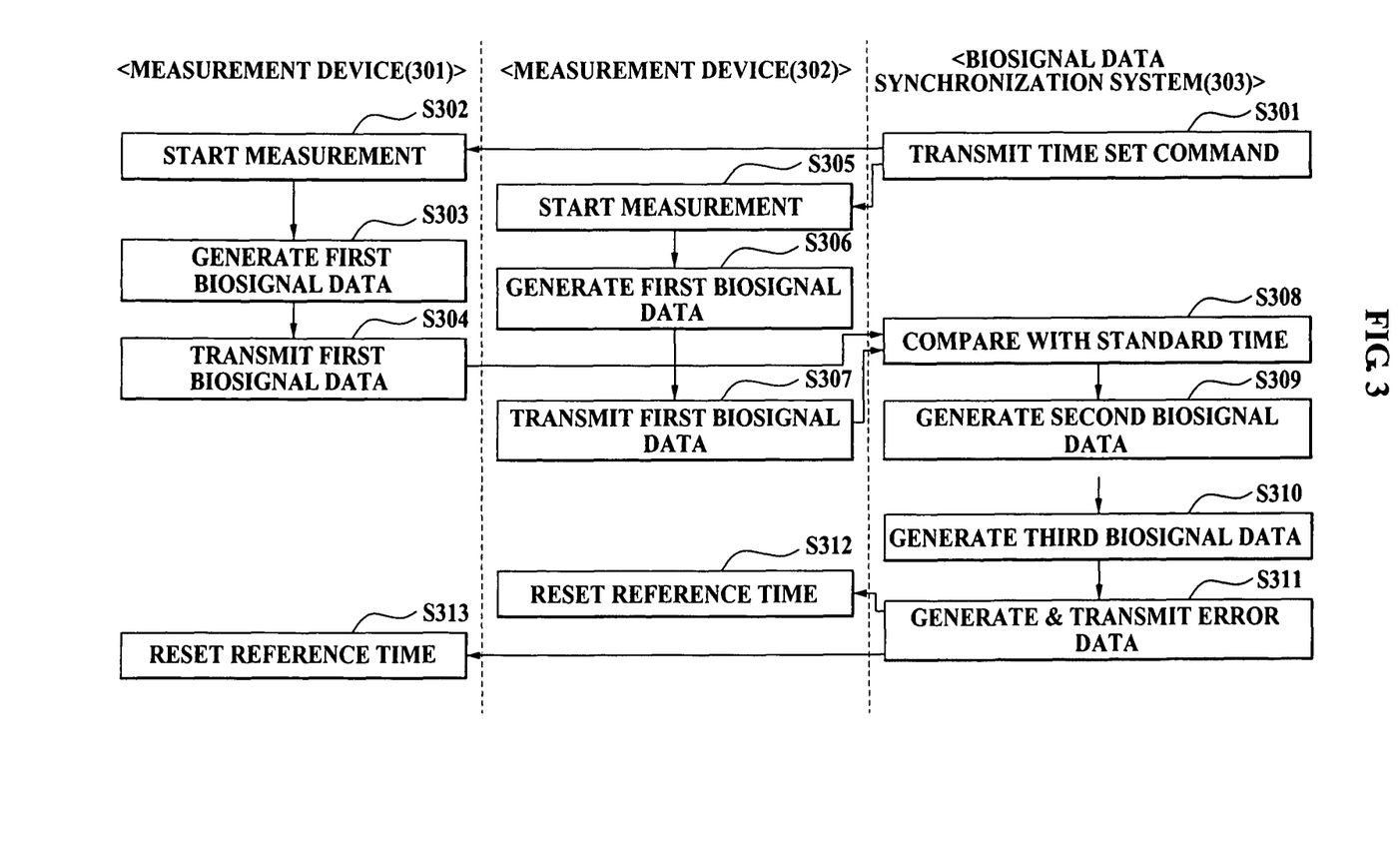
FIG. 3 is a flowchart illustrating a process of synchronizing biosignal data according to an exemplary embodiment of the present invention.

FIG. 3 is a flowchart illustrating a process of synchronizing biosignal data according to an exemplary embodiment of the present invention. Referring to FIG. 3, the process of synchronizing biosignal data according to the present exemplary embodiment will be described.

In operation S301, a biosignal data synchronization system 303 according to the present exemplary embodiment transmits a time set command to each of a plurality of measurement devices 301 and 302. In this instance, the time set command includes information enabling the measurement device 301 and 302 to start measuring.

In operation S302, the measurement device 301 receives the time set command and, in response thereto, measures a user's biosignal from a measurement start time to a measurement termination time and generates first biosignal data.

The measurement start time may be a time when the time set command is received or a pre-set time. Also, the measurement termination time may be a pre-set time or a time included in the time set command.

In this instance, the measurement device 301 records a data value corresponding to a time axis and generates first biosignal data in operation S303. Also, the time axis includes a measurement start time and a measurement termination time.

Figure 4A:
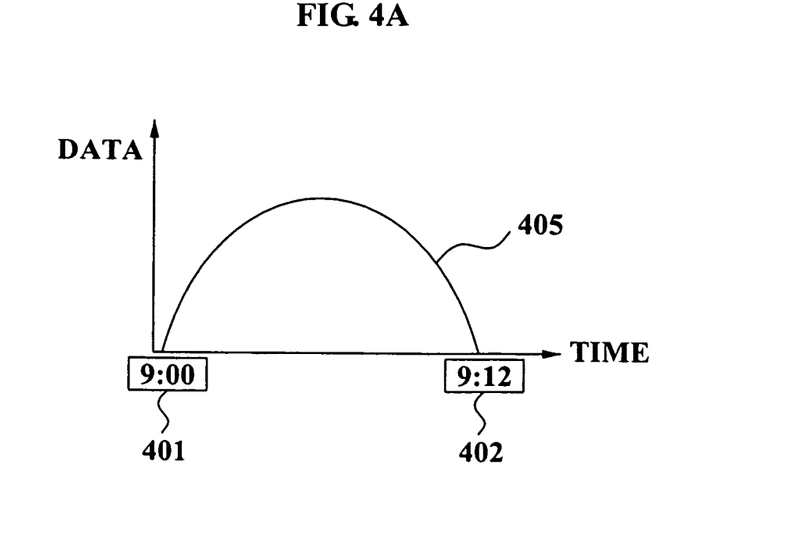
FIGS. 4A and 4B are diagrams illustrating first biosignal data generated in a measurement device according to an exemplary embodiment of the present invention.
Figure 4B:
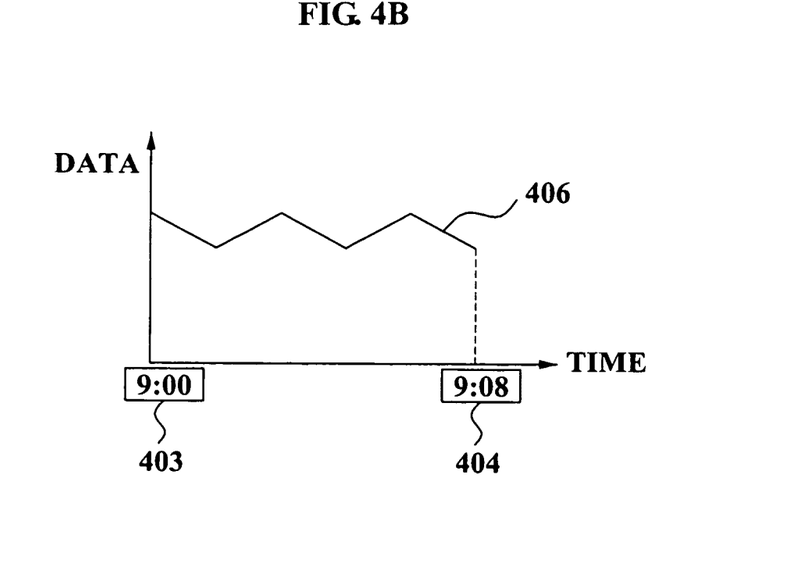

FIGS. 4A and 4B are diagrams illustrating first biosignal data generated in a measurement device according to an exemplary embodiment of the present invention.

Referring to FIG. 4A, the measurement device 301 records a data value corresponding to a time axis and generates first biosignal data. In this instance, the time axis includes a measurement start time 401 and a measurement termination time 402.

As an example, the measurement device 301 measures a user's "activity pattern" from the measurement start time "9:00" 401 to the measurement termination time "9:12" 402, thereby generating first biosignal data 405.

The measurement device 302 of FIG. 3 also receives the time set command in operation S305, and generates first biosignal data in operation S306.

As an example, as illustrated in FIG. 4B, the measurement device 301 may measure a user's "electrocardiogram" from a measurement start time "9:00" 403 to a measurement termination time "9:08" 404, thereby generating first biosignal data 406.

In operation S304 of FIG. 3, when the measurement is completed, the measurement device 301 transmits the generated first biosignal data to the biosignal data synchronization system 303.

In operation S307, when measurement is completed, the measurement device 302 also transmits the generated first biosignal data to the biosignal data synchronization system 303.

In operation S308, the biosignal data synchronization system 303 receives first biosignal data and compares the measurement start time and the measurement termination time of first biosignal data with a standard time.

As an example, the biosignal data synchronization system 303 compares the measurement start time "9:00" 401 and the measurement termination time "9:12" 402 of the first biosignal data 405, as illustrated in FIG. 4A, with a standard time. In this instance, the standard time follows a standard clock installed in the biosignal data synchronization system 303.

In the above-described example, when the standard time of "9:00" is identical to the corresponding measurement start time "9:00" 401 of the first biosignal data 405, but the standard time of "9:10" is not identical to the corresponding measurement termination time "9:12" 402 of the first biosignal data 405, the reference time of the measurement terminal 301 is determined to have an error.

A standard time corresponding to a measurement start time may be a point in time when a time set command is transmitted from the biosignal data synchronization system 303. Also, the standard time may be a time which is obtained by summing up a transmission period of the time set command and the point in time when the time set command is transmitted.

A standard time corresponding to a measurement termination time may be a point in time when first biosignal data is received in the biosignal data synchronization system 303. Also, the standard time may be a time which is obtained by subtracting a transmission period of the first biosignal data from the point in time when the first biosignal data is received.

The biosignal data synchronization system 303 may compare the measurement start time "9:00" 403 and the measurement termination time "9:08" 404 of the first biosignal data 406, as illustrated in FIG. 4B, with a standard time and determine whether there is an error.

In operation S309, when the comparison results in an error, the biosignal data synchronization system 303 generates second biosignal data from corrected first biosignal data, corrected by referring to the standard time. In this instance, the biosignal data synchronization system 303 corrects a time axis of the first biosignal data by referring to the standard time and generates the second biosignal data.

In the above-described example, when the standard time of "9:00" is identical to the corresponding measurement start time "9:00" 401 of the first biosignal data 405, but the standard time of "9:10" is not identical to the corresponding measurement termination time "9:12" 402 of the first biosignal data 405, the biosignal data synchronization system 303 corrects the measurement termination time of the first biosignal data in the time axis, from "9:12" to "9:10", and generates the second biosignal data.

Figure 5A:
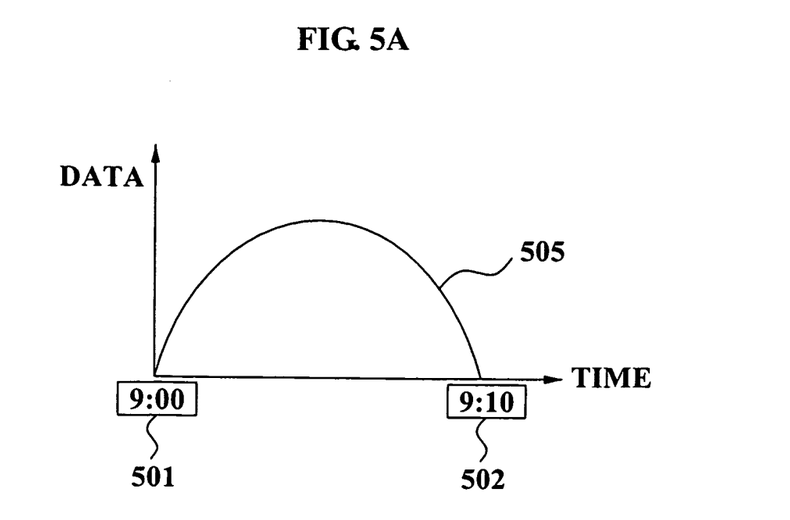
FIGS. 5A and 5B are diagrams illustrating second biosignal data generated by correcting first biosignal data in a biosignal data synchronization system according to an exemplary embodiment of the present invention.
Figure 5B:
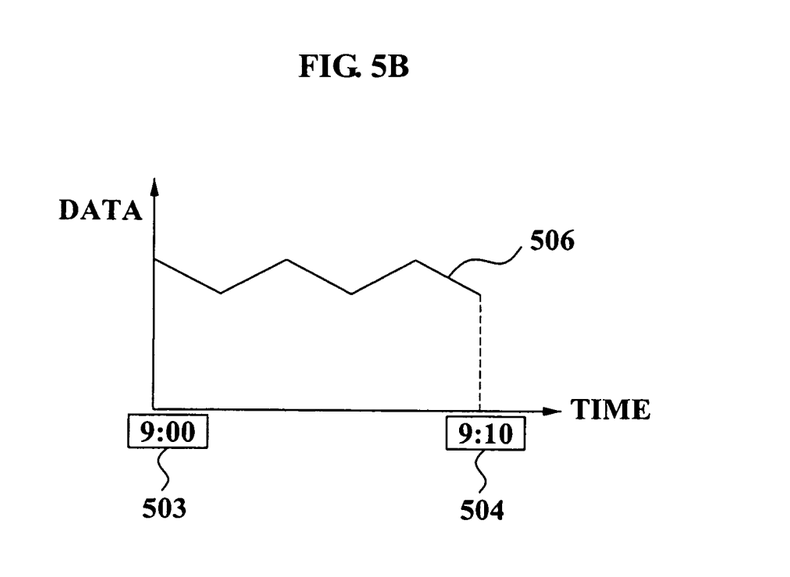

FIGS. 5A and 5B are diagrams illustrating second biosignal data generated by correcting first biosignal data in a biosignal data synchronization system according to an exemplary embodiment of the present invention.

Referring to FIG. 5A, the biosignal data synchronization system corrects the time axis of the first biosignal data 405 which is received from the measurement device 301, and generates second biosignal data 505 corresponding to the standard time. Namely, the second biosignal data 505 is generated by correcting the time axis so that the measurement termination time "9:12" 402 of the first biosignal data 405 becomes "9:10" 502.

Also, referring to FIG. 5B, the biosignal data synchronization system corrects the time axis of the first biosignal data 406 which is received from the measurement device 302, and generates the second biosignal data 506 corresponding to the standard time. Namely, the biosignal data synchronization system corrects the measurement termination time of the first biosignal data 406, in the time axis, that is, from "9:08" 404 to "9:10" 504, and generates the second biosignal data 506.

In operation S310 of FIG. 3, the biosignal data synchronization system 303 synchronizes a plurality of the second biosignal data and generates third biosignal data.

In this instance, when the biosignal data synchronization system 303 is installed in a measurement device, the second biosignal data may be data which is measured in the measurement device including the biosignal data synchronization system 303. Also, in this case, the second biosignal data may be synchronized with other second biosignal data without a time error correction process, to generate third biosignal data.

Figure 6:
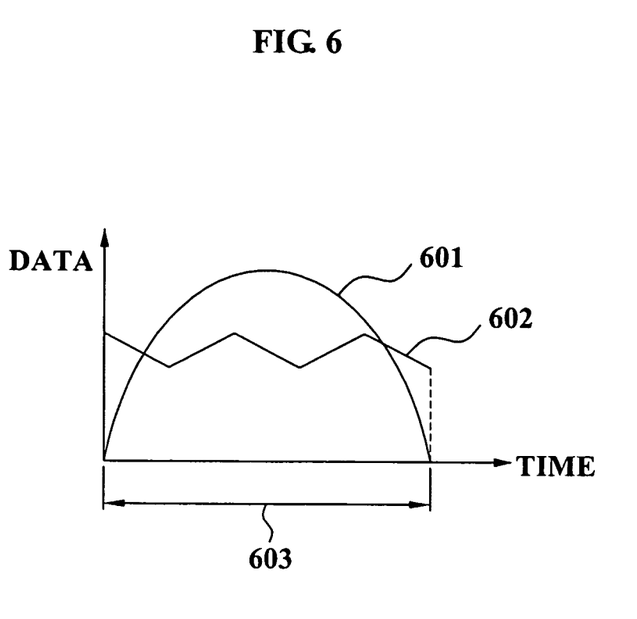
FIG. 6 is a diagram illustrating third biosignal data generated by synchronizing second biosignal data according to an exemplary embodiment of the present invention.

FIG. 6 is a diagram illustrating third biosignal data generated by synchronizing second biosignal data according to an exemplary embodiment of the present invention.

Referring to FIG. 6, the biosignal data synchronization system 303 synchronizes a plurality of second biosignal data 601 and 602 to be matched in an identical axis and generates third biosignal data. Reference numeral 603 refers to standard time in an exemplary embodiment.

As an example, when the second biosignal data 601 is associated with a user's "activity pattern" and the second biosignal data 602 is associated with the user's "electrocardiogram", the second biosignal data 601 and 602 are synchronized to be matched in the time axis. Accordingly, it is possible to check and analyze the user's health from a change of "electrocardiogram" according to the user's "activity pattern" by referring to third biosignal data.

Namely, the present invention generates second biosignal data by correcting a time error of first biosignal data received from a plurality of measurement devices, and synchronizes the plurality of second biosignal data to match in an identical time axis. Accordingly, although an error exists in the reference time of the measurement device, it is possible to synchronize and generate biosignal data by accurately correcting the error.

Also, the present invention synchronizes various biosignal data received from a plurality of measurement devices without a time error, and provides the synchronized biosignal data. Accordingly, it is possible to provide third biosignal data which can analyze a user's health from various pattern changes of biosignals in an identical time.

In operation S311 of FIG. 3, the biosignal data synchronization system 303 generates error data with respect to the error, and transmits the generated error data to the measurement device.

In the above-described example, the biosignal data synchronization system 303 may generate error data including information, such as "reference time is 2 minutes fast", and transmit the generated error data to the measurement device 301. Also, the biosignal data synchronization system 303 may generate error data including information, such as "reference time is 2 minutes slow", and transmits the generated error data to the measurement device 302.

In operations S312 and S313, the measurement devices 301 and 302 may correct a reference time error by receiving the error data and resetting their reference time according to the error data.

In the above-described example, when error data including information, such as "reference time is 2 minutes fast", is received from the biosignal data synchronization system 303, the measurement device 301 resets its reference time back 2 minutes. Also, when error data including information, such as "reference time is 2 minutes slow", is received from the biosignal data synchronization system 303, the measurement device 302 resets its reference time ahead 2 minutes. In this manner, the reference time may be set to be identical to the standard time of the biosignal data synchronization system 303.

Namely, according to the present invention, it is possible to correct an error in a timer installed in a measurement device and set a reference time to be identical to a standard time of a biosignal data synchronization system.

Figure 7:
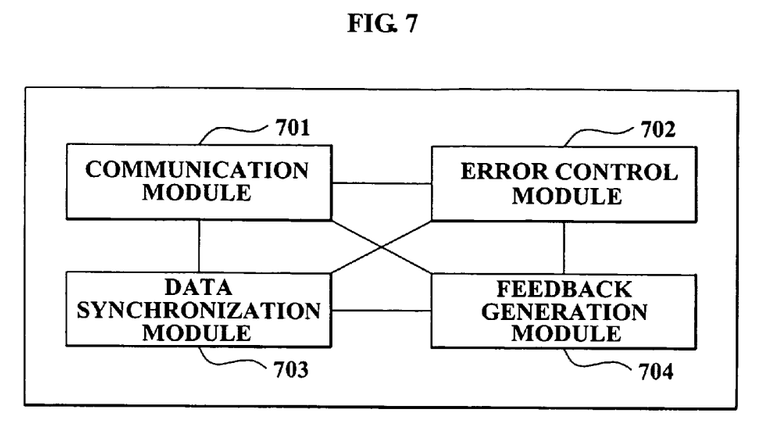
FIG. 7 is a block diagram illustrating a configuration of a biosignal data synchronization system according to an exemplary embodiment of the present invention.

FIG. 7 is a block diagram illustrating a configuration of a biosignal data synchronization system according to an exemplary embodiment of the present invention.

Referring to FIG. 7, the biosignal data synchronization system according to the present exemplary embodiment includes a communication module 701, an error control module 702, a data synchronization module 703, and a feedback generation module 704.

The communication module 701 transmits a time set command to each of a plurality of measurement devices and receives a user's first biosignal data from each of the plurality of the measurement devices. In this instance, as described above, the first biosignal data includes a time axis and the time axis includes a measurement start time and a measurement termination time.

The error control module 702 compares the measurement start time and the measurement termination time with a standard time. When the comparison results in an error, the error control module 702 generates second biosignal data from corrected first biosignal data, corrected by referring to the standard time. An exemplary embodiment describing the generated second biosignal data has been described above with reference to FIGS. 5A and 5B.

In this instance, the error control module 702 may generate the second biosignal data by correcting the time axis of the first biosignal data with reference to the standard time.

The data synchronization module 703 synchronizes a plurality of the second biosignal data and generates third biosignal data. The generated third biosignal data has been described above with reference to FIG. 6.

The feedback generation module 704 generates error data with respect to the error and transmits the generated error data to the measurement device.

Figure 8:
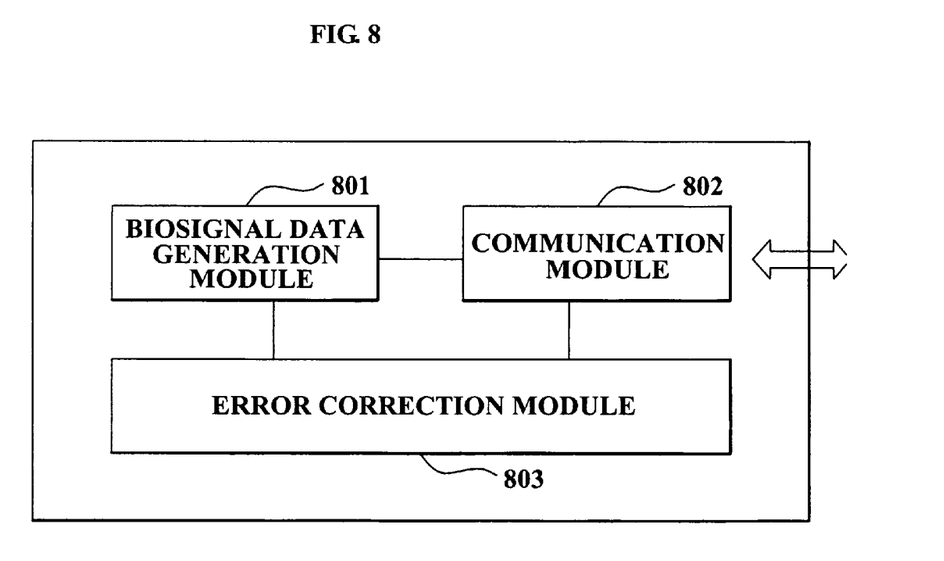
FIG. 8 is a block diagram illustrating a configuration of a measurement device according to an exemplary embodiment of the present invention.

FIG. 8 is a block diagram illustrating a configuration of a measurement device according to an exemplary embodiment of the present invention.

Referring to FIG. 8, the measurement device according to the present exemplary embodiment includes a biosignal generation module 801, a communication module 802, and an error correction module 803.

The biosignal data generation module 801 receives a time set command from a biosignal data synchronization system, and in response to the received time set command, measures a user's biosignal and generates first biosignal data.

The communication module 802 transmits the generated first biosignal data to the biosignal data synchronization system.

The error correction module 803 receives error data from the biosignal data synchronization system and corrects a reference time of the measurement device.

In this instance, as described above, the biosignal data synchronization system receives the user's first biosignal data from the measurement device, compares a measurement start time and a measurement termination time with a standard time of the system, when the comparison results in an error, generates second biosignal data from corrected measurement data, corrected by referring to the standard time, and generates the error data with respect to the error and transmits the generated error data to the measurement device.

The biosignal data synchronization system and the measurement device according to the above-described exemplary embodiments of the present invention have been previously described. The above-described exemplary embodiments may be applied to the biosignal data synchronization system and the measurement device of FIGS. 7 and 8. Accordingly, detailed description related thereto will be omitted herein.

According to the above-described exemplary embodiments of the present invention, a biosignal data synchronization method and system can accurately correct an error in a reference time of a measurement device and generate synchronized biosignal data, by correcting a time error of first biosignal data received from a plurality of measurement devices, generating second biosignal data and synchronizing the second biosignal data to match in an identical time axis.

Also, according to the above-described exemplary embodiments of the present invention, a biosignal data synchronization method and system can provide third biosignal data enabling analysis of a user's health on the basis of various pattern changes of biosignals within an identical time, by synchronizing and providing various biosignal data received from a plurality of measurement devices without a time error.

Also, according to the above-described exemplary embodiments of the present invention, a biosignal data synchronization method and system can correct an error of a timer installed in a measurement device and set a reference time to be identical to a standard time of a biosignal data synchronization system.

In addition to the above-described exemplary embodiments, exemplary embodiments of the present invention can also be implemented by executing computer readable code/instructions in/on a medium/media, e.g., a computer readable medium/media. The medium/media can correspond to any medium/media permitting the storing and/or transmission of the computer readable code/instructions. The medium/media may also include, alone or in combination with the computer readable code/instructions, data files, data structures, and the like. Examples of instructions include both machine code, such as produced by a compiler, and files containing higher level code that may be executed by the computer using an interpreter.

The computer readable code/instructions can be recorded/transferred in/on a medium/media in a variety of ways, with examples of the medium/media including magnetic storage media (e.g., floppy disks, hard disks, magnetic tapes, etc.), optical media (e.g., CD-ROMs, or DVDs), magneto-optical media (e.g., floptical disks), hardware storage devices (e.g., read only memory media, random access memory media, flash memories, etc.) and storage/transmission media such as carrier waves transmitting signals, which may include computer readable code/instructions, data files, data structures, etc. Examples of storage/transmission media may include wired and/or wireless transmission (such as transmission through the Internet). Examples of wired storage/transmission media may include optical wires/lines, metallic wires/lines, and waveguides. The medium/media may also be a distributed network, so that the computer readable code/instructions is stored/transferred and executed in a distributed fashion. The computer readable code/instructions may be executed by one or more processors. In addition, the above hardware devices may be configured to act as one or more software modules in order to perform the operations of the above-described exemplary embodiments.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A method of synchronizing a user's biosignal data received from a plurality of measurement devices, comprising:

transmitting a time set command to each of the plurality of measurement devices;

receiving the user's first biosignal data from each of the plurality of measurement devices, the first biosignal data including a time axis and the time axis including a measurement start time and a measurement termination time;

comparing the measurement start time and the measurement termination time with a standard time; and generating second biosignal data from corrected first biosignal data, corrected by referring to the standard time, when the comparison results in an error; and synchronizing the second biosignal data and generating third biosignal data, wherein each of the plurality of measurement devices receives the time set command and generates the first biosignal data, and wherein the measurement start time causes the beginning of the measuring of the biosignal data, and the measurement termination time causes, or is caused by, the completion of the measuring of the biosignal data.

2. The method of claim 1, wherein, in the generating second biosignal data, the second biosignal data is generated by correcting a time axis of the first biosignal data by referring to the standard time.

3. The method of claim 1, further comprising:

generating error data with respect to the error and transmitting the generated error data to the measurement device, wherein the measurement device receives the error data and resets a reference time of the measurement device.

4. A method of operating a measurement device measuring a user's biosignal and generating biosignal data, comprising:

receiving a time set command from a predetermined system and, in response to receipt of the time set command, measuring the user's biosignal, and generating first biosignal data, the first biosignal data including a time axis and the time axis including a measurement start time and a measurement termination time;

transmitting the generated biosignal data to the system; and receiving error data from the system and resetting a reference time of the measurement device, wherein the measurement start time causes the beginning of the measuring of the biosignal data, and the measurement termination time causes, or is caused by, the completion of the measuring of the biosignal data, wherein the system receives the user's first biosignal data from the measurement device, the first biosignal data including a time axis and the time axis including a measurement start time and a measurement termination time, compares the measurement start time and the measurement termination time with the standard time of the system, and when the comparison results in an error, generates second biosignal data from corrected measurement data, corrected by referring to the standard time, and generates error data with respect to the error and transmits the generated error data to the measurement device.

5. A computer readable recording medium storing a program for implementing a method of synchronizing a user's biosignal data received from a plurality of measurement devices, the method comprising:
transmitting a time set command to each of the plurality of measurement devices;
receiving the user's first biosignal data from each of the plurality of measurement devices, the first biosignal data including a time axis and the time axis including a measurement start time and a measurement termination time;
comparing the measurement start time and the measurement termination time with a standard time;
generating second biosignal data from corrected first biosignal data, corrected by referring to the standard time, when the comparison results in an error; and
generating third biosignal data by synchronizing a plurality of the second biosignal data,
wherein each of the plurality of measurement devices receives the time set command and generates the first biosignal data, and
wherein the measurement start time causes the beginning of the measuring of the biosignal data, and the measurement termination time causes, or is caused by, the completion of the measuring of the biosignal data.

6. A system for synchronizing a user's biosignal data received from a plurality of measurement devices, comprising:
a communication module to transmit a time set command to each of the plurality of measurement devices and to receive the user's first biosignal data from each of the plurality of measurement devices, the first biosignal data including a time axis and the time axis including a measurement start time and a measurement termination time;
an error control module to compare the measurement start time and the measurement termination time with a standard time and, when the comparison results in an error, to generate second biosignal data from corrected first biosignal data, corrected by referring to the standard time, and
a data synchronization module to synchronize a plurality of the generated second biosignal data and to generate third biosignal data based on synchronization of the plurality of second biosignal data,
wherein the measurement start time causes the beginning of the measuring of the biosignal data, and the measurement termination time causes, or is caused by, the completion of the measuring of the biosignal data.

7. The system of claim 6, wherein the error control module corrects the time axis of the first biosignal data by referring to the standard time.

8. The system of claim 7, further comprising a feedback generation module to generate error data with respect to the error and to transmit the generated error data to each of the plurality of measurement devices,
wherein each of the plurality of measurement devices receives the error data and resets a standard time of each of the plurality of measurement devices.

9. A device of measuring a user's biosignal and generating biosignal data, comprising:
a biosignal data generation module to receive a time set command from a predetermined system and, in response to the received time set command, to measure the user's biosignal, and to generate first biosignal data, the first biosignal data including a time axis and the time axis including a measurement start time and a measurement termination time;
a communication module to transmit the generated first biosignal data to the system; and
an error correction module to receive error data from the system and to correct a reference time of the measurement device,
wherein the system receives the user's first biosignal data from the measurement device, the first biosignal data including a time axis and the time axis including a measurement start time and a measurement termination time, compares the measurement start time and the measurement termination time with a standard time of the system, when the comparison results in an error, generates second biosignal data from corrected measurement data, corrected by referring to the standard time, synchronizes second biosignal data, generates third biosignal data based on the synchronized second biosignal data, and generates error data with respect to the error and transmits the generated error data to the measurement device, and
wherein the measurement start time causes the beginning of the measuring of the biosignal data, and the measurement termination time causes, or is caused by, the completion of the measuring of the biosignal data.

10. A method of synchronizing a user's biosignal data received from a plurality of measurement devices, comprising:
transmitting a time set command to each of the plurality of measurement devices;
receiving the user's first biosignal data from each of the plurality of measurement devices, the first biosignal data including a time axis and the time axis including a measurement start time and a measurement termination time;
comparing the measurement start time and the measurement termination time with a standard time; and
generating second biosignal data from corrected first biosignal data, corrected by referring to the standard time, when the comparison results in an error;
synchronizing the second biosignal data; and
generating third biosignal data based on synchronization of second biosignal data,
wherein the measurement start time causes the beginning of the measuring of the biosignal data, and the measurement termination time causes, or is caused by, the completion of the measuring of the biosignal data.

11. At least one computer readable medium storing instructions that control at least one processor to implement a method of synchronizing a user's biosignal data received from a plurality of measurement devices, the method comprising:
transmitting a time set command to each of the plurality of measurement devices;

receiving the user's first biosignal data from each of the plurality of measurement devices, the first biosignal data including a time axis and the time axis including a measurement start time and a measurement termination time;

comparing the measurement start time and the measurement termination time with a standard time;

generating second biosignal data from corrected first biosignal data, corrected by referring to the standard time, when the comparison results in an error;

synchronizing a plurality of the second biosignal data; and generating third biosignal data based on synchronization of the plurality of second biosignal data, wherein the measurement start time causes the beginning of the measuring of the biosignal data, and the measurement termination time causes, or is caused by, the completion of the measuring of the biosignal data.

12. A method of synchronizing a user's biosignal data received from a plurality of measurement devices, comprising:

transmitting a time set command to each of the plurality of measurement devices;

receiving the user's first biosignal data from each of the plurality of measurement devices, the first biosignal data including a time axis and the time axis including a measurement start time and a measurement termination time;

comparing the measurement start time and the measurement termination time with a standard time; and generating second biosignal data from corrected first biosignal data, corrected by referring to the standard time, when the comparison results in an error;

synchronizing a plurality of the second biosignal data; and generating third biosignal data based on the synchronization of the plurality of second biosignal data.

13. At least one computer readable medium storing instructions that control at least one processor to implement a method of synchronizing a user's biosignal data received from a plurality of measurement devices, the method comprising:

transmitting a time set command to each of the plurality of measurement devices;

receiving the user's first biosignal data from each of the plurality of measurement devices, the first biosignal data including a time axis and the time axis including a measurement start time and a measurement termination time;

comparing the measurement start time and the measurement termination time with a standard time;

generating second biosignal data from corrected first biosignal data, corrected by referring to the standard time, when the comparison results in an error;

synchronizing a plurality of the second biosignal data; and generating third biosignal data based on synchronization of the plurality of second biosignal data.

14. A system for synchronizing a user's biosignal data received from a plurality of measurement devices, comprising:

a communication module to transmit a time set command to each of the plurality of measurement devices and to receive the user's first biosignal data from each of the plurality of measurement devices, the first biosignal data including a time axis and the time axis including a measurement start time and a measurement termination time;

an error control module to compare the measurement start time and the measurement termination time with a standard time and, when the comparison results in an error, to generate second biosignal data from corrected first biosignal data, corrected by referring to the standard time, and a data synchronization module to synchronize a plurality of the generated second biosignal data and to generate third biosignal data based on synchronization of the plurality of second biosignal data.

* * * * *